United States Patent [19]

Corley

[11] Patent Number: 4,935,571

[45] Date of Patent: Jun. 19, 1990

[54] PROCESS FOR THE PURIFICATION OF CYCLOBUTENOARENES

[75] Inventor: Larry S. Corley, Houston, Tex.

[73] Assignee: Shell Oil Company, Houston, Tex.

[21] Appl. No.: 238,390

[22] Filed: Aug. 31, 1988

[51] Int. Cl.$^5$ .......................... C07C 13/06; C07C 7/17
[52] U.S. Cl. ...................................... 585/410; 585/866
[58] Field of Search ............... 585/866, 809, 811, 833, 585/836, 866, 410

[56] References Cited

U.S. PATENT DOCUMENTS

| | | | |
|---|---|---|---|
| 3,306,946 | 2/1967 | Synder et al. | 585/809 X |
| 4,540,763 | 9/1985 | Kirchoff | 526/281 |
| 4,544,782 | 10/1985 | Chapman et al. | 585/443 |
| 4,851,603 | 7/1989 | Quarderer et al. | 585/410 |

OTHER PUBLICATIONS

Chapman et al., J. Am. Chem. Soc., 1987, 109, 553–559.
Rabjohn, J. Am. Chem. Soc., 1954, 76, 5579–5481.

*Primary Examiner*—Glenn Caldarola

[57] ABSTRACT

A process for the recovery of a cyclobutenoarene such as benzocyclobutene from a mixed reaction product is disclosed. The mixed reaction product is contacted with an aqueous acid solution so as to convert impurities to species such as oligomers and water addition products which have sufficiently reduced volatility that they can be separated from cyclobutenoarene by distillation. The cyclobutenoarene is then recovered from the organic phase.

16 Claims, No Drawings

PROCESS FOR THE PURIFICATION OF CYCLOBUTENOARENES

BACKGROUND OF THE INVENTION

This invention relates to the preparation of cyclobutenoarenes. In a specific aspect, the invention relates to the purification of benzocyclobutenes prepared by the pyrolysis of o-methylbenzyl halides.

The four-membered ring of benzocyclobutenes is known to open at elevated temperature to form a very reactive diene which rapidly dimerizes and polymerizes. Molecules containing two or more benzocyclobutene groups are therefore useful as heat-curable thermosetting resins. Also, elastomers or thermoplastics containing benzocyclobutene substituents crosslink on heating. In order to economically prepare such useful benzocyclobutenefunctional resins or polymers, however, an economic method of generating the benzocyclobutene structure in pure form is needed. In the past, the benzocyclobutene structure has been synthesized most commonly by pyrolysis of substituted or unsubstituted o-methylbenzyl halides at temperatures above 650° C. and pressures below 2 mm Hg.

Benzocyclobutenes produced by vacuum pyrolysis tend to be quite heavily contaminated with isomeric styrenes and the phenylacetylenes formed by dehydrogenation of the styrenes. Formation of styrene and phenylacetylene tends to be a particularly severe problem at pyrolysis tube temperatures of 800° to 900° C., at which the highest conversions of o-methylbenzyl halides to benzocyclobutene per pass are obtained.

Because of their similar boiling points, styrenes and phenylacetylenes are extremely difficult to separate from benzocyclobutenes by distillation. For example, benzocyclobutene boils at 146°–148° C. at atmospheric pressure, while the boiling points of styrene and phenylacetylene are 145°–146° C. and 142°–44° C., respectively. If the styrene and phenylacetylene are not removed from the benzocyclobutene, problems tend to occur in subsequent functionalization reactions for the preparation of precursors of bisbenzocyclobutene resins or benzocyclobutene-functional monomers.

For example, a standard method of benzocyclobutene functionalization involves initial bromination of the side chain. If the benzocyclobutene undergoing bromination contains styrene or phenylacetylene, these impurities tend to form di- or tetrabromides, respectively, under the bromination conditions. Such side-chain brominated materials tend to lose HBr at the high pot temperatures of the subsequent distillation procedure. The HBr damages the vacuum pump, and HBr elimination also yields monobromostyrenes, which boil at temperatures close to the bromobenzocyclobutene product and hence contaminate the distilled material.

It would thus be desirable to find new methods to recover benzocyclobutene from a reaction product mixture containing benzocyclobutene and similar-boiling by-products such as styrene and phenylacetylene.

SUMMARY OF THE INVENTION

According to the invention, crude cyclobutenoarene is contacted with an aqueous acid solution under conditions effective to convert organic impurities such as isomeric styrenes and/or phenylacetylene into less volatile compounds, such as hydrated forms or oligomers of such compounds, which can be separated from the cyclobutenoarene by distillation. In a preferred embodiment, a crude pyrolysis reaction product mixture containing benzocyclobutene is contacted with an aqueous solution of concentrated sulfuric acid for a time effective to chemically convert the styrene and phenylacetylene impurities into a mixture of oligomers and water addition products such as alcohols and ketones, which are less volatile than the benzocyclobutene and from which the benzocyclobutene can be separated by distillation.

DETAILED DESCRIPTION OF THE INVENTION

The invention process involves the separation of a cyclobutenoarene from a reaction product mixture which includes the cyclobutenoarene and at least one other similar-boiling compound. In a specific embodiment, the invention involves the recovery of benzocyclobutene from a pyrolysis reaction product mixture which includes various aromatic by-products of pyrolysis, such as styrene and phenylacetylene. For simplicity, the invention will be discussed in terms of such a pyrolysis reaction product mixture from which benzocyclobutene is recovered, with the understanding that the invention applies generally to the separation of cyclobutenoarenes from similar-boiling contaminants.

In the recovery of benzocyclobutene from a pyrolysis product mixture, the product mixture is contacted with an aqueous acid solution. The acid solution contains a sufficient acid concentration to effect hydration, or other addition reactions, on the contaminant materials, e.g., hydration of the double bond of styrene or the triple bond of phenylacetylene. The acid solution must not be so strong, however, as to cause extensive loss of benzocyclobutene through attack on the aromatic ring (for example, sulfonation) or opening of the four-membered ring. At extremely high acid concentration, such side reactions will occur to such an extent that the acid phase will not separate from the organic phase on standing, and an emulsion will form if additional water is added in an attempt to force phase separation.

Suitable acids include strong inorganic acids, such as sulfuric acid, alkane or arene sulfonic acids, $HBF_4$, $HPF_6$ and $HSbF_6$, for example. The preferred acid, because of its commercial availability and demonstrated effectiveness, is sulfuric acid. Preferred aqueous acid solutions for the invention process are mixtures of 100 parts by weight commercial concentrated sulfuric acid (95-98 percent $H_2SO_4$) with about 8 to about 25 parts by weight of water. The amount of aqueous acid solution used can range from about 5 to about 300 weight percent, based on the weight of the crude reaction product mixture, preferably from about 10 to about 100 weight percent.

In order to effect recovery of the benzocyclobutene from the reaction product mixture, the crude benzocyclobutene is mixed with the aqueous acid solution with agitation to promote intimate contact between the organic phase and the acid phase, for a time sufficient to convert a substantial portion of any styrene and phenylacetylene present to higher-boiling products. With good agitation, a contact time of about one to two hours will generally be sufficient, although this will vary, with shorter contact times possible with more vigorous agitation, higher temperature, and higher acid concentration in the aqueous phase. It is preferred to carry out the reaction at or slightly above room temperature, generally from about 20° to about 70° C., and atmospheric pressure, although higher or lower temperatures and pressures may sometimes be useful. The contacting of the reaction product mixture with the acid solution results in a two-phase organic/aqueous system in which the organic phase contains the benzocyclobutene and the products of hydration or other conversion reactions of aromatic by-products present in the reaction product mixture, and the aqueous phase contains the acid.

The organic phase is then separated from the aqueous phase. To facilitate separation of the phases and removal of acid from the organic phase, additional water may be added to the system prior to phase separation. After optional drying of the recovered organic phase, pure benzocyclobutene is recovered from the organic phase by distillation or other separation technique.

The invention purification process can be employed in the preparation of cyclobutenoarenes by the pyrolysis of o-alkylarylmethyl halides at temperatures above about 650° C. and pressures below about 2 mm Hg. A mixed pyrolysis product stream is passed to a condensation zone wherein product cyclobutenoarene, unreacted starting material and pyrolysis by-products such as isomeric styrenes and phenylacetylenes are condensed, preferably in the presence of water for aqueous condensation of HCl, as a liquid product mixture. The mixture can be subjected to distillation to separate the cyclobutenoarene (accompanied by styrenes and phenylacetylenes present) from unreacted starting material The impure cyclobutenoarene can then be treated according to the above-described process for recovery of purified cyclobutenoarene from such by-products as styrene and phenylacetylene. Preferably, however, the crude pyrolysis product containing cyclobutenoarene, styrene, phenylacetylene and o-alkylarylmethyl halide is treated with aqueous acid as the first step of cyclobutenoarene purification. The acid will convert the styrene and phenylacetylene to less volatile materials without significantly affecting the cyclobutenoarene or o-alkylbenzyl halide starting material. The mixture can then, after optional drying, be distilled directly to provide a pure cyclobutenoarene fraction.

EXAMPLE 1

This example illustrates the use of sulfuric acid-water mixtures for removing styrene and phenylacetylene from benzocyclobutene (BCB) and the effect of water concentration on the effectiveness of such removal. A series of mixtures of reagent grade concentrated sulfuric acid (95.8% $H_2SO_4$) and water were prepared as shown in Table 1 below. Subsequently, 1.5 grams of each sulfuric acid-water mixture were mixed in a glass vial with 5 grams of a batch of crude benzocyclobutene (o-methylbenzyl chloride pyrolysis product). The vials were shaken vigorously and then placed on a tumbler for two hours at room temperature (approximately 25° C.).

At the end of the two-hour period, an amount of water (usually 1.5 grams) was added to each mixture in order to increase the volume of the aqueous phase and make it easier to separate from the organic phase. (Separation became more difficult with decreasing water concentration in the sulfuric acid solution used for the original treatment, possibly because of sulfonation of some of the aromatic rings. More water had to be added to separate the phases in some of these materials, and some formed emulsions which could not be separated at all.) The phases were then separated and the organic phase was dried over calcium oxide. The organic phase—calcium oxide mixtures were centrifuged and the organic phase was decanted and analyzed by gas chromatography. Results are shown in Table 1 below.

TABLE 1

| | Composition of aqueous acid: | | Volume of water added for phase sepn., mL | Organic phase composition, GC peak area %[a] | | | | |
|---|---|---|---|---|---|---|---|---|
| Run # | g conc. $H_2SO_4$ | g water | | BCB | Phenyl-acetylene | Styrene | o-Xylene | o-Methylbenzyl chloride |
| 1 | 10 | 0 | 5[b] | | | | | |
| 2 | 10 | 0.5 | 5[b] | | | | | |
| 7 | 10 | 0.75 | 4 | 38.77 | 0.04 | | 0.84 | 39.15 |
| 3 | 10 | 1.0 | 1.5 | 41.35 | 0.04 | 0.02 | 0.82 | 38.10 |
| 4 | 10 | 1.5 | 1.5 | 46.52 | 0.03 | | 0.82 | 39.93 |
| 8 | 10 | 2.0 | 1.5 | 45.30 | 0.03 | | 0.79 | 38.96 |
| 5 | 10 | 2.5 | 1.5 | 46.79 | 1.25 | 1.34 | 0.81 | 38.99 |
| 6 | 10 | 4.0 | 1.5 | 47.06 | 3.22 | 2.36 | 0.82 | 38.00 |

[a]Gas chromatographic conditions: 60 meter column, 0.25 mm diameter, coated with 0.25 μm thick film of Supelco SPB-5; nitrogen carrier gas (200 kPa gauge pressure, 120 mL/min split flow, ratio = ~200:1); initial temp. 40° C.; final temp. 300° C.; heating rate 5° C./min.; injector temp. 220° C.; flame ionization detector, detector temp. 280° C.; sample dissolved at 1.5% in isooctane, 2 μL injected using autosampler.
[b]Formed stable emulsion which would not separate on standing.

From the data in Table 1, it can be seen that, for the conditions described, there is an optimum range of water concentration in the aqueous sulfuric acid mixtures for purification of crude benzocyclobutene. If the water concentration is too high (runs 5 and 6, Table 1), substantial amounts of styrene and phenylacetylene remain in the treated solution, with the amounts of unreacted styrene and phenylacetylene increasing with increasing water concentration. If the water concentration is too low (runs 1 and 2, Table 1), the system forms an emulsion (probably from sulfonation of the benzocyclobutene) and the aqueous acid phase cannot be mechanically separated from the organic phase, even when large amounts of water are added. At optimum intermediate water concentrations in the aqueous acid phase, very little unreacted styrene and phenylacetylene remain but the two phases can be easily separated. Near the lower boundary of optimum water concentration (runs 7 and 3, Table 1) some of the benzocyclobutene appears to be lost to sulfonation or other reactions as shown by the lowered relative size of the benzocyclobutene gas chromatographic peak. Within this region, the benzocyclobutene loss increases with decreasing water concentration.

EXAMPLE 2

This example shows the effect of contact time on styrene and phenylacetylene removal from crude benzocyclobutene by a mixture of 100 parts of reagent grade concentrated sulfuric acid (95.8% $H_2SO_4$) and 15 parts of water. Three sample vials (as in Example 1) were each filled with 2.5 grams of this aqueous acid mixture and 10 grams of the same crude benzocyclobutene mixture used in Example 1. The vials were shaken vigorously, placed on a rotating tumbler, and tumbled for different lengths of time at room temperature. Three grams of water were then added to each mixture and the aqueous and organic phases were mechanically separated. The organic phase was dried over calcium oxide, separated from the calcium oxide by centrifugation, and then analyzed by gas chromatography (conditions given in footnote to Table 1). Results are shown in Table 2 below.

of the crude material. (Compositions of distillation cuts after cut #6 are not shown, since these consisted predominantly of the starting material, o-methylbenzyl chloride, which is significantly less volatile than benzocyclobutene, styrene and phenylacetylene.)

TABLE 3

| Cut # | Boiling range, °C.[a] begin | Boiling range, °C.[a] end | Volume %[b] | Cut composition, GC peak area %[c] BCB | Phenyl acetylene | Styrene | o-Xylene | o-Methylbenzyl chloride |
|---|---|---|---|---|---|---|---|---|
| CT[e] | | | 1.8 | | | | | |
| 1 | 151 | 153 | 5.2 | 68.9 | 17.1 | 8.1 | 3.8 | |
| 2 | 153 | 154 | 5.2 | 85.1 | 7.8 | 4.8 | 1.6 | |
| 3 | 154 | 154 | 4.5 | 89.5 | 5.4 | 3.7 | 1.1 | |
| 4 | 154 | 154 | 10.6 | 93.8 | 3.0 | 2.5 | 0.6 | |
| 5 | 154 | 154 | 10.7 | 98.3 | 0.6 | 0.8 | 0.1 | |
| 6 | 154 | 206 | 11.3 | 45.3 | 0.03 | 0.06 | | 41.6 |
| 7 | 206 | 204 | 6.2 | | | | | |
| 8 | 204 | 205 | 6.2 | | | | | |
| 9 | 205 | 206 | 6.0 | | | | | |
| 10 | 206 | 206 | 13.2 | | | | | |
| 11 | 206 | 205 | 5.9 | | | | | |
| KR[d] | | | 26.5 | | | | | |

[a]Corrected to one atmosphere pressure.
[b]Volume percentages add to over 100%, possibly because of expansion due to demixing which accompanies distillation.
[c]Gas chromatographic conditions were same as in footnote (a) of Table 1.
[d]Kettle residue after distillation.
[e]Material collected in dry ice trap during distillation.

TABLE 2

| Run # | Contact time between organic phase and aqueous acid solution, minutes | Organic phase composition, GC peak area %[a] BCB | Phenyl-acetylene | Styrene | o-Xylene | o-Methylbenzyl chloride |
|---|---|---|---|---|---|---|
| 1 | 20 | 47.09 | 2.90 | 2.07 | 0.82 | 37.92 |
| 2 | 40 | 48.10 | 0.36 | 0.35 | 0.83 | 39.24 |
| 3 | 80 | 47.23 | 0.04 | 0.03 | 0.82 | 39.78 |

[a]Gas chromatographic conditions same as in footnote (a) to Table 1.

One can see from Table 2 that, for the conditions described, a contact time of an hour or more gave best removal of styrene and phenylacetylene with little if any increased loss of benzocyclobutene.

COMPARATIVE EXAMPLE 3

A batch of crude benzocyclobutene (approximately 3700 mL in volume) was prepared by combining the organic phases from a series of vacuum pyrolyses of o-methylbenzyl chloride. The crude benzocyclobutene contained 38.5% benzocyclobutene, 2.0% phenylacetylene, 1.2% styrene, 0.4% o-xylene, and 48.0% o-methylbenzyl chloride by gas chromatography (conditions given in footnote to Table 1). The mixture was mixed with 5% of EPON ® Resin 828 (a nonvolatile scavenger for any HCl which would be formed during the distillation). It was then distilled at approximately 20 mm Hg (2700 Pa) at a 10:1 reflux ratio through a 30-plate Oldershaw column 5.1 cm in diameter. The distillation results are given in Table 3 below.

As shown in Table 3, most of the distillation cuts containing predominantly benzocyclobutene were heavily contaminated with styrene and phenylacetylene. Only in one benzocyclobutene cut (cut #5) were the concentrations of each of these two impurities each below 1%. This cut contained less than 11% by volume

EXAMPLE 3

A batch of crude benzocyclobutene was prepared by combining the organic phases from a series of vacuum pyrolyses of o-methylbenzyl chloride and performing a simple distillation to remove nonvolatile impurities. The crude benzocyclobutene contained 48.9% benzocyclobutene, 3.6% phenylacetylene, 2.6% styrene, 0.8% o-xylene, and 39.8% o-methylbenzyl chloride by gas chromatography (conditions given in footnote to Table 1). A 1000-gram portion of the crude benzocyclobutene was then mixed with a blend of 250 grams commercial concentrated $H_2SO_4$ and 37.5 grams water in a bottle with vigorous magnetic stirring. The temperature had risen to 55° C. approximately 5 minutes after the crude benzocyclobutene and aqueous acid were mixed. Thirty minutes after mixing, the temperature of the mixture had risen to 62° C. although no external heat was applied. Additional water (300 g) was then added to the mixture and the aqueous and organic layers were allowed to separate. The organic layer was then dried over calcium oxide.

Analysis by gas chromatography (conditions given in footnote to Table 1) showed that the acid-treated organic layer contained 41.0% benzocyclobutene, 0.04% phenylacetylene, 0.85% o-xylene, and 36.6% o-methylbenzyl chloride, with styrene undetectable. The acid-treated organic layer was mixed with 5% of EPON ® Resin 828 (a nonvolatile scavenger for any HCl which would be formed during the distillation) and was then distilled at approximately 20 mm Hg (2700 Pa) at a 4:1 reflux ratio through a 30-plate Oldershaw column 2.54 cm in diameter. The distillation results are given in Table 4 below.

One can see that styrene and phenylacetylene contamination was almost nonexistent in the benzocyclobutene cuts obtained by distillation of the acid-treated material. Styrene and phenylacetylene were not regenerated to any significant degree in the distillation pot from the products of their previous reaction with aqueous acid. (As in Table, #3, composition of distillation cuts after cut #5 are not shown, since these consisted predominantly of the starting material, o-methylbenzyl chloride, which is a significantly less volatile than benzocyclobutene, styrene or phenylacetylene.)

TABLE 4

| Cut # | Boiling range, °C.[a] begin | Boiling range, °C.[a] end | Volume %[b] | Cut composition, GC peak area %[c] BCB | Cut composition, GC peak area %[c] Phenyl acetylene | Cut composition, GC peak area %[c] Styrene | Cut composition, GC peak area %[c] o-Xylene | Cut composition, GC peak area %[c] o-Methylbenzyl chloride |
|---|---|---|---|---|---|---|---|---|
| CT[e] | | | 0.2 | | | | | |
| 1 | 149 | 152 | 5.2 | 89.73 | 0.36 | | 6.97 | |
| 2 | 152 | 152 | 4.6 | 96.39 | 0.09 | | 2.81 | |
| 3 | 152 | 151 | 9.6 | 98.57 | 0.02 | | 1.17 | |
| 4 | 151 | 153 | 10.5 | 99.01 | | 0.02 | 0.27 | |
| 5 | 153 | 202 | 4.9 | 54.90 | | 0.03 | 0.03 | 27.65 |
| 6 | 202 | 203 | 5.9 | | | | | |
| 7 | 203 | 203 | 5.1 | | | | | |
| 8 | 203 | 203 | 4.9 | | | | | |
| 9 | 203 | 203 | 5.2 | | | | | |
| 10 | 203 | 203 | 5.3 | | | | | |
| 11 | 203 | 202 | 5.7 | | | | | |
| 12 | 202 | 185 | 2.5 | | | | | |
| KR[d] | | | 39.0 | | | | | |

[a]Corrected to one atmosphere pressure.
[b]Volume percentages add to over 100%, possibly because of expansion due to demixing which accompanies distillation.
[c]Gas chromatographic conditions were same as in footnote (a) of Table 1.
[d]Kettle residue after distillation.
[e]Material collected in dry ice trap during distillation.

I claim:

1. A process for treating a cyclobutenoarene reaction product mixture comprising a cyclobutenoarene and aromatic impurities, the process comprising the steps of
   (a) contacting said cyclobutenoarene reaction product mixture with an aqueous acid solution under effective conditions to produce an organic phase containing the cyclobutenoarene and hydrated forms of the aromatic impurities, and an aqueous phase containing the acid;
   (b) separating the organic phase and the aqueous phase; and
   (c) recovering the cyclobutenoarene from the organic phase.

2. The process of claim 1 in which the cyclobutenoarene is benzocyclobutene.

3. The process of claim 1 in which the reaction product mixture is a product of pyrolysis of an o-alkylarylmethyl halide.

4. The process of claim 1 in which the acid is concentrated sulfuric acid.

5. The process of claim 4 in which the aqueous acid solution is a mixture of concentrated sulfuric acid and from about 8 to about 25 weight percent water, based on the weight of the concentrated sulfuric acid.

6. The process of claim 2 in which the reaction product mixture comprises at least one of styrene and phenylacetylene.

7. The process of claim 1 in which said contacting is effected at a temperature within the range of from about 20° to about 70° C. and at atmospheric pressure.

8. A process for preparing a cyclobutenoarene comprising the steps of
   (a) introducing into a pyrolysis zone a starting material comprising an o-alkylarylmethyl halide and water;
   (b) subjecting said starting material to pyrolysis conditions and producing a pyrolysis product mixture comprising a cyclobutenoarene and at least one aromatic by-product;
   (c) passing the pyrolysis product mixture to a condensation zone and producing a condensation product comprising a liquid cyclobutenoarene and the at least one aromatic by-product;
   (d) contacting said condensation product with an aqueous acid solution under conditions effective to produce an organic phase containing cyclobutenoarene and products of reaction of the acid with at least one aromatic by-product and an aqueous phase containing sulfuric acid; and
   (e) recovering the cyclobutenoarene.

9. The process of claim 8 in which the cyclobutenoarene is benzocyclobutene.

10. The process of claim 8 in which the o-alkylarylmethyl halide is an o-methylbenzyl halide.

11. The process of claim 8 in which the acid is sulfuric acid.

12. The process of claim 8 in which the aqueous acid solution is a mixture of concentrated sulfuric acid and from about 8 to about 25 weight percent water, based on the weight o: the concentrated sulfuric acid.

13. The process of claim 9 in which the pyrolysis product mixture comprises at least one of styrene and phenylacetylene.

14. The process of claim 8 in which said contacting of step (d) is carried out at a temperature of from about 20° to about 70° C. and atmospheric pressure.

15. The process of claim 8 in which the aqueous acid solution is present in an amount of from about 10 to about 100 weight percent, based on the weight of the pyrolysis product mixture.

16. The process of claim 8 in which the cyclobutenoarene is recovered by distillation.

* * * * *